United States Patent [19]

Becker

[11] Patent Number: 5,004,651

[45] Date of Patent: Apr. 2, 1991

[54] STABILIZING SYSTEM FOR SOLID DOSAGE FORMS

[75] Inventor: Wallace E. Becker, Franksville, Wis.

[73] Assignee: Abbott Laboratories, Abbott Park, Ill.

[21] Appl. No.: 301,579

[22] Filed: Jan. 24, 1989

[51] Int. Cl.$^5$ .............................................. A61K 9/20
[52] U.S. Cl. .................................... 424/465; 424/468; 424/496
[58] Field of Search ................ 424/468, 465; 514/530, 514/496

[56] References Cited

U.S. PATENT DOCUMENTS

| | | | |
|---|---|---|---|
| 4,409,239 | 10/1983 | Yu | 514/530 |
| 4,410,545 | 10/1983 | Yu | 514/530 |
| 4,829,083 | 5/1989 | Doulakas | 514/669 |

*Primary Examiner*—Thurman K. Page
*Assistant Examiner*—Leon R. Horne
*Attorney, Agent, or Firm*—Steven R. Crowley; Steven F. Weinstock

[57] ABSTRACT

An improved pharmaceutical preparation uses tromethamine and dibasic potassium phosphate or calcium carbonate to enhance stability.

14 Claims, No Drawings

STABILIZING SYSTEM FOR SOLID DOSAGE FORMS

TECHNICAL FIELD

The present invention relates to solid dosage forms of pharmaceutical preparations and more particularly to pharmaceutical preparations having increased stability.

BACKGROUND OF THE INVENTION

Some drugs are not stable by themselves or in an acid environment, and require an alkaline environment. In addition, such drugs may possess insufficient solubility and require the use of buffers to obtain complete solubilization prior to processing by conventional wet granulation methods. Furthermore, the buffer can increase the thermal stability of the drug formulation during the drying step of the granulation process.

For example, estropipate is an estrogenic substance (piperazine estrone sulfate) indicated for the treatment of estroqen deficiency in females. Estropipate is unstable in an acid environment or when combined with lactose which is considered an inert pharmaceutical excipient. Excess piperazine has been used to provide an alkaline environment for stabilizing estropipate tablet dosage forms. The excess piperazine also ensures solubilization of the estrone sulfate in the granulating media to ensure a uniform distribution of the drug during the wet granulation process.

A disadvantage of utilizing piperazine is that it is volatile and susceptible to loss when utilizing vacuum drying, which because of environmental considerations is the preferred method of processing granulations containing potent drugs.

Another disadvantage of piperazine is that it is a strong base and may have an adverse effect on excipients used with estropipate. For example, lactose discolors and emits a carmelized odor in the presence of piperazine.

SUMMARY OF THE INVENTION

The pharmaceutical formulation of the present invention is a solid dosage form having a unique buffer system that utilizes tromethamine (2-amino-2-hydroxymethyl-1,3-propanediol). Tromethamine has surprisingly been found to have excellent stabilizing effects on solid dosage forms containing drugs with limited water solubility which need to be solubilized in buffer to avoid otherwise solubilizing the drug in large quantities of granulating media. Tromethamine has been discovered to be most advantageous when a therapeutically effective, buffer-soluble drug has a solubility at 25° C. of less than 1 mg of drug per ml of water at pH 7.0 or lower. Once solubilized, the pharmaceutical preparation can be combined with excipients, granulated, vacuum dried and lubricated within a conventional, closed processing system, typically referred to as a solids processor. See, for example, Scarpone et al., *Pharmaceutical Technology*, pp. 44–52, September, 1986. Accordingly, with the formulation of the invention, the active ingredient(s) or excipients of the formulation are not exposed to the work place and yet the uniformity and appearance of the active drug ingredient are maintained.

The foregoing features and advantages of the present invention will be further understood upon consideration of the following detailed description of the preferred embodiments.

DETAILED DESCRIPTION OF THE PREFERRED EMBODIMENTS

The pharmaceutical formulations of the present invention provide a stable environment for drugs which require an alkaline environment by utilizing tromethamine as a buffer. Such formulations also may contain an excipient as a major component that functions as a carrier for the active ingredients. Examples of suitable excipients include sucrose, mannitol, lactose, magnesium oxide, calcium carbonate, calcium sulfate, magnesium carbonate, tribasic calcium phosphate and dibasic calcium phosphate.

It has been found that the stability of the estropipate is enhanced when the formulation includes an additional alkaline buffering agent. Thus, in one preferred embodiment, the formulation contains a water soluble alkaline excipient as a minor component that functions as a secondary buffering agent. For example, dibasic potassium phosphate is soluble in water and, accordingly, blends well with an excipient like lactose. Anhydrous dibasic potassium phosphate USP is the preferred form of potassium phosphate. Examples of other suitable buffering agents include sodium acetate, dibasic sodium phosphate and combinations of sodium or potassium hydroxide with sodium or potassium acid phosphate.

Surprisingly, it has also been found that alkaline excipients that are insoluble in water may also be used without any detrimental effect on the stability of the tablet. Examples of such insoluble alkaline excipients include calcium carbonate, tribasic calcium phosphate, magnesium oxide, magnesium hydroxide and magnesium carbonate.

The manufacture of tablet dosage forms of the invention typically includes dissolving dibasic potassium phosphate in water and using the solution to granulate a mixture of lactose, color, hydroxypropyl cellulose, sodium starch glycolate and cellulose microcrystalline. The resultant base product is then dried employing conventional methods. Next, the active ingredient, e.g. estropipate, is dissolved in alcohol and purified water along with tromethamine. The estropipate solution is then mixed with the base excipient to form a granulation. This resultant product is then vacuum dried (although other conventional drying methods may be used); mixed with colloidal silicon dioxide, magnesium stearate and hydrogenated vegetable oil wax to lubricate and then compressed into tablets.

Each tablet in the above procedure preferably contains a therapeutically effective amount of estropipate, typically from 0.375 to 6.00 mg, from about 50 to about 750 mg sugar excipient, e.g., lactose, from about 0.5 to 2.5 mg (Lake) dye, from about 0.1 to about 10 mg dibasic potassium phosphate, from about 0.1 to 10 mg tromethamine, from about 3 to about 30 mg hydroxypropyl cellulose, from about 5 to about 45 mg sodium starch glycolate, from about 25 to about 150 mg microcrystalline cellulose, from about .25 to about 3.0 mg colloidal silicon dioxide, from about 0.5 to about 7.5 mg magnesium stearate, and from about 0.5 to about 7.5 mg wax. The lactose and dibasic potassium phosphate may be replaced with from 50 mg to 750 mg calcium carbonate or another alkaline calcium salt.

The manufacture of estropipate tablets using the stabilizing system of the presently preferred embodiments of the present invention is illustrated by the following examples:

EXAMPLE 1

Tablets containing 1.5 mg of estropipate are made with the ingredients and amounts as follows:

| Ingredient | Quantity for 1,000 Tablets (gm) |
| --- | --- |
| Lactose, Monohydrate | 144.8 |
| Color | 1 |
| Dibasic Potassium Phosphate | 1 |
| Hydroxypropyl Cellulose | 9 |
| Sodium Starch Glycolate | 10 |
| Microcrystalline Cellulose | 50 |
| Purified Water | -qs- |

Dibasic potassium phosphate is first dissolved in water. Lactose, color, hydroxypropyl cellulose, sodium starch glycolate, and microcrystalline cellulose are then charged into a mass mixture, and granulated with the dibasic potassium phosphate solution. The granulation is then dried employing conventional methods and passed through a 30 mesh screen.

| Ingredient | Quantity for 1,000 Tablets (gm) |
| --- | --- |
| Estropipate | 1.5 |
| Tromethamine | 1.2 |
| Alcohol SD 3A 200 | -qs- |
| Purified Water | -qs- |

Tromethamine and estropipate are dissolved in approximately 90% alcohol and 10% purified water. Approximately 30 ml of solvent per 1000 tablets is used. The base granulation is charged into a solids processor and massed with the tromethamine/estropipate solution. The wet granulation is vacuum dried to a moisture content of not more than 2%.

| Ingredient | Quantity for 1,000 Tablets (gm) |
| --- | --- |
| Colloidal Silcon Dioxide | 0.5 |
| Magnesium Stearate | 1 |
| Wax, Hydrogenated | 1 |

The dried resultant granulation is then lubricated, discharged into bins and compressed into tablets in any conventional manner.

EXAMPLE 2

In the same manner as described in Example 1, a tablet containing 0.75 mg of estropiate is made with the ingredients and amounts indicated below.

| Ingredient | Quantity for 1,000 Tablets (gm) |
| --- | --- |
| Estropipate | 0.75 |
| Lactose | 145.5 |
| D&C Yellow Dye No. 10 Lake | 1.0 |
| FD&C Yellow Dye No. 6 Lake | 0.01 |
| Dibasic Potassium Phosphate | 1.0 |
| Tromethamine | 1.2 |
| Hydroxypropyl Cellulose NF | 9.0 |
| Sodium Starch Glycolate | 10.0 |
| Cellulose Microcrystalline, NF | 50.0 |
| *Water | -qs- |
| *Alcohol | -qs- |
| Colloidal Silicon Dioxide | 0.5 |
| Magnesium Stearate | 1.0 |
| Wax | 1.0 |

*Removed during processing.

EXAMPLE 3

In the same manner as described in Example 1, a tablet containing 3.0 mg of estropiate is made with the ingredients and amounts indicated below.

| Ingredient | Quantity for 1,000 Tablets (gm) |
| --- | --- |
| Estropipate | 3.0 |
| Lactose | 143.8 |
| FD&C Blue Dye No. 2 Lake | 0.50 |
| Dibasic Potassium Phosphate | 1.0 |
| Tromethamine | 1.2 |
| Hydroxypropyl Cellulose NF | 9.0 |
| Sodium Starch Glycolate | 10.0 |
| Cellulose Microcrystalline, NF | 50.0 |
| *Water | -qs- |
| *Alcohol | -qs- |
| Colloidal Silicon Dioxide | 0.5 |
| Magnesium Stearate | 1.0 |
| Wax | 1.0 |

*Removed during processing.

EXAMPLE 4

In the same manner as described in Example 1, a tablet containing 6.00 mg of estropiate is made with the ingredients and amounts indicated below.

| Ingredient | Quantity for 1,000 Tablets (gm) |
| --- | --- |
| Estropipate | 6.00 |
| Lactose | 140.1 |
| D&C Yellow Dye No. 10 Lake | 1.0 |
| D&C Blue Dye No. 2 Lake | 0.25 |
| Dibasic Potassium Phosphate | 1.0 |
| Tromethamine | 1.2 |
| Hydroxypropyl Cellulose NF | 9.0 |
| Sodium Starch Glycolate | 10.0 |
| Cellulose Microcrystalline, NF | 50.0 |
| *Water | -qs- |
| *Alcohol | -qs- |
| Colloidal Silicon Dioxide | 0.5 |
| Magnesium Stearate | 1.0 |
| Wax | 1.0 |

*Removed during processing.

EXAMPLE 5

A formulation utilizing calcium carbonate as both an excipient and alkaline stabilizer (replacing lactose and dibasic potassium phosphate in Example 2) is shown below.

| Ingredient | Quantity for 1,000 Tablets (gm) |
| --- | --- |
| Estropipate | 0.75 |
| Calcium Carbonate | 750 |
| D&C Yellow Dye No. 10 Lake | 3 |
| FD&C Yellow Dye No. 6 Lake | 0.02 |
| Tromethamine | 1.2 |
| Hydroxypropyl Cellulose NF | 30 |
| Sodium Starch Glycolate, NF | 45 |
| Cellulose Microcrystalline, NF | 150 |
| *Water | -qs- |
| *Alcohol | -qs- |

| Ingredient | Quantity for 1,000 Tablets (gm) |
| --- | --- |
| Colloidal Silicon Dioxide | 3 |
| Magnesium Stearate | 7.5 |
| Wax | 7.5 |

*Removed during process

Calcium carbonate, microcrystalline cellulose, sodium starch glycolate, hydroxypropyl cellulose, dye yellow D&C No. 10 Lake and dye yellow FDC No. 6 Lake are charged into the solids processor. If necessary, powders are screened or milled to break up glomerates. A portion of the microcrystalline cellulose may be added at the lubrication step. Tromethamine and estropipate are dissolved in purified water/alcohol. The powders are granulated with tromethamine/estropipate solution. The wet granulation is vacuum dried to a moisture content of not more than Colloidal silicon dioxide, magnesium stearate and hydrogenated vegetable oil wax are added to the granulation. The materials are blended and discharged into bins. If necessary, the lubricated granulation may be screened and/or milled when ed from the solids processor.

The resultant granulation is compressed on rotary tableting machine using ovaloid tooling.

Estropipate Tablet Stability

Estropipate tablets without buffer and with either piperazine or a combination of tromethamine and potassium phosphate dibasic or tromethamine and calcium carbonate were compared in an accelerated stability test.

The tablets were exposed to 90 grains of water per pound of dry air at 77° C. (70% relative humidity) until the equilibrated LOD (loss on drying) was 1.5 percent. Prior to exposure and conditioning, the LOD values were approximately 0.5 percent. The tablets were then exposed to a temperature of 80° C. for 7 days in a Blue M, Stabil-Therm ® gravity convection oven. At the end of 7 days at 80° C., the amount of estropipate that had degraded to estrone was determined by HPLC analysis. The results of this test are shown in Table 1.

TABLE 1

Stability of 1.5 mg Estropipate Tablets Under Accelerated Storage Conditions (80° C., 7 days)

| Buffer | Percent Degradation to Estrone | |
| --- | --- | --- |
| None | 51.1 | (Average of 6 tests) |
| Piperazine (1.2 mg/tablet) | 3.5 | |
| Tromethamine/K$_2$HPO$_4$ (1.2/1.0 mg/tablet) | 1.6 | |
| Tromethamine/CaCO$_3$ (1.2/250 mg/tablet) | 1.6 | |

The results of this test indicate that an alkaline environment increases the stability of estropipate tablets. The results also indicate that replacing piperazine as the buffer with a tromethamine buffer increases the stability of estropipate tablets.

Although the present invention has been described in connection with presently preferred embodiments, those skilled in the art will recognize many modifications to sequence, arrangement, portions, elements, and materials which can be used in the practice of the invention without departing from its scope. It is intended that such changes and modifications be covered by the following claims.

What is claimed is:

1. A pharmaceutical preparation in a solid dosage form comprising estropipate and tromethamine in a weight ratio of estropipate to triomethamine from about 0.375 to about 6.0

2. The preparation of claim 1 further comprising a supplemental alkaline stabilizer.

3. The preparation of claim 2 further comprising an excipient.

4. The preparation of claim 3 wherein the supplemental alkaline stabilizer is dibasic potassium phosphate and the excipient is a sugar.

5. The preparation of claim 4 wherein the excipient is lactose.

6. The preparation of claim 3 wherein the excipient and supplemental alkaline stabilizer is calcium carbonate.

7. A pharmaceutical preparation in solid dosage form comprising:
  a therapeutically effective amount of estropipate; an amount of tromethamine effective for stabilizing the estropipate, said amount being selected from the range 0.1 mg to 10 mg of tromethamine;
  50 mg to 750 mg lactose; and
  0.1 mg to 10 mg dibasic potassium diphosphate.

8. The preparation of claim 7 comprising 0.375–6.00 mg of estropipate.

9. A pharmaceutical preparation is solid dosage form comprising:
  a therapeutically effective amount of estropipate; an amount of tromethamine effective for stabilizing the estropipate, said amount being selected from the range 0.1 mg to 10 mg of tromethamine; and
  750 mg calcium carbonate.

10. The preparation of claim 9 comprising 0.375–6.00 mg of estropipate.

11. A method for stabilizing estropipate in a solid pharmaceutical dosage form comprising the step of admixing tromethamine to the estropipate.

12. A pharmaceutical preparation in solid dosage form comprising:
  0.375 mg to 6.0 mg of estropipate;
  an amount of tromethamine effective for stabilizing the estropipate, said amount being selected from the range 0.1 mg to 10 mg of tromethamine;
  50 mg, to 750 mg of lactose; and
  0.1 mg to 10 mg of dibasic potassium diphosphate.

13. A pharmaceutical preparation in solid dosage form comprising:
  0.375 mg of 6.0 mg of estropipate; an amount of tromethamine effective for stabilizing the estropipate,
  said amount being selected from the range 0.1 mg to 10 mg of tromethamine; and 50 mg to 750 mg of calcium carbonate.

14. A pharmaceutical preparation in solid dosage form comprising:
  0.375 mg to 6.0 mg of estropiate;
  1.2 mg of tromethamine; and
  1.0 mg of dibasic potassium diphosphate.

* * * * *

UNITED STATES PATENT AND TRADEMARK OFFICE
CERTIFICATE OF CORRECTION

PATENT NO. : 5,004,651

DATED : April 2, 1991

INVENTOR(S) : Wallace E. Becker

It is certified that error appears in the above-identified patent and that said Letters Patent is hereby corrected as shown below:

COLUMN 5, LINE 11:  Replace "FDC" with --FD&C--.

COLUMN 5, LINE 13:  Replace "break up" with --break-up--.

COLUMN 5, LINE 19:  After "than" insert --2.0%--.

COLUMN 5, LINE 21:  AFTER "the" insert --dried--.

COLUMN 5, LINE 24:  Replace "ed" with --discharged--.

COLUMN 5, LINE 35:  Replace "90" with --98--.

COLUMN 5, LINE 36:  After "C" delete --.--.

COLUMN 5, LINE 40:  After "C" delete --.--.

COLUMN 5, LINE 42:  After "C" delete --.--.

COLUMN 5, LINE 48:  After "C" delete --.--.

COLUMN 5, Line 13, "glomerates" should be --agglomerates--.

UNITED STATES PATENT AND TRADEMARK OFFICE
CERTIFICATE OF CORRECTION

PATENT NO. : 5,004,651

DATED : April 2, 1991

INVENTOR(S) : Wallace E. Becker

It is certified that error appears in the above-identified patent and that said Letters Patent is hereby corrected as shown below:

COLUMN 6, LINE 7: Before "estropipate" insert

--0.375-6.0 mg--.

COLUMN 6, LINE 7: Before "tromethamine" insert

--0.1 to 10 mg--.

COLUMN 6, LINES 7-9: Delete "in a weight ratio of estropipate to triomethamine from about 0.375 to about 6.0".

COLUMN 6, LINE 33: Replace "is" with --in--.

COLUMN 6, LINE 39: Before "750" insert --50 mg to--.

COLUMN 6, LINE 51: After "mg" delete--,--.

Signed and Sealed this

Second Day of March, 1993

Attest:

STEPHEN G. KUNIN

Attesting Officer

Acting Commissioner of Patents and Trademarks